US011065446B2

(12) United States Patent
Oh et al.

(10) Patent No.: US 11,065,446 B2
(45) Date of Patent: Jul. 20, 2021

(54) GLASSES-SHAPED COCHLEAR IMPLANT DEVICE

(71) Applicants: Seoul National University R&DB Foundation, Seoul (KR); Todac Co., Ltd., Seoul (KR)

(72) Inventors: Seung Ha Oh, Seoul (KR); Sung June Kim, Seoul (KR); Jin Ho Kim, Seoul (KR); Jeong Hoan Park, Seoul (KR); Tae Mok Gwon, Seoul (KR); Chae Bin Kim, Seoul (KR)

(73) Assignees: Seoul National University R&DB Foundation, Seoul (KR); Todae Co., Ltd., Seoul (KR)

( * ) Notice: Subject to any disclaimer, the term of this patent is extended or adjusted under 35 U.S.C. 154(b) by 0 days.

(21) Appl. No.: 15/576,882

(22) PCT Filed: May 26, 2016

(86) PCT No.: PCT/KR2016/005589
§ 371 (c)(1),
(2) Date: Nov. 27, 2017

(87) PCT Pub. No.: WO2016/190685
PCT Pub. Date: Dec. 1, 2016

(65) Prior Publication Data
US 2018/0147412 A1 May 31, 2018

(30) Foreign Application Priority Data

May 26, 2015 (KR) .................. 10-2015-0073066

(51) Int. Cl.
*A61N 1/00* (2006.01)
*A61N 1/36* (2006.01)
*H04R 25/00* (2006.01)
*G02C 11/06* (2006.01)
*H04R 1/02* (2006.01)
(Continued)

(52) U.S. Cl.
CPC ....... *A61N 1/36038* (2017.08); *A61N 1/0541* (2013.01); *A61N 1/3787* (2013.01);
(Continued)

(58) Field of Classification Search
CPC ........ A61N 1/36038; G02B 2027/0178; H04R 25/606
See application file for complete search history.

(56) References Cited

U.S. PATENT DOCUMENTS 6,265,100 B1 * 7/2001 Saaski ............... H01M 10/0431
429/161
6,308,101 B1 * 10/2001 Faltys .................. A61N 1/3787
607/57
(Continued)

FOREIGN PATENT DOCUMENTS

KR 10-2006-0001786 1/2006
KR 20-0416313 5/2006
(Continued)

OTHER PUBLICATIONS

International Search Report and the Written Opinion dated Aug. 24, 2016 From the Korean Intellectual Property Office Re. Application No. PCT/KR2016/005589 and Its Translation of Search Report Into English. (9 Pages).

*Primary Examiner* — Rex R Holmes
*Assistant Examiner* — Sana Sahand

(57) ABSTRACT

Provided is a cochlear implant device with a glasses shape. The disclosed cochlear implant device improves body wearability and aesthetic effects by designing the cochlear implant device to have a glasses shape, and achieves alignment of a receiver coil implanted into the body and a transmission coil outside the body without using a magnet because the transmission coil is integrally provided at an end of a glasses temple such that a region of a body with which
(Continued)

the transmission coil comes into contact is changed according to a bending degree of the glasses temple.

6 Claims, 5 Drawing Sheets

(51) Int. Cl.
    *A61N 1/05*          (2006.01)
    *A61N 1/372*        (2006.01)
    *A61N 1/378*        (2006.01)
    *G02B 27/01*        (2006.01)

(52) U.S. Cl.
    CPC ..... *A61N 1/37229* (2013.01); *G02B 27/0172* (2013.01); *G02C 11/06* (2013.01); *H04R 1/028* (2013.01); *H04R 25/554* (2013.01); *G02B 2027/0178* (2013.01); *H04R 25/606* (2013.01); *H04R 2225/67* (2013.01)

(56) References Cited

U.S. PATENT DOCUMENTS

| | | | | |
|---|---|---|---|---|
| 7,937,156 B2* | 5/2011 | Gibson | ................ | A61N 1/0541 607/57 |
| 8,352,046 B1* | 1/2013 | Haller | ................ | H04R 25/552 607/137 |
| 9,544,675 B2* | 1/2017 | Facteau | ................ | H04R 23/008 |
| 2002/0019669 A1* | 2/2002 | Berrang | ............. | A61N 1/36036 623/10 |
| 2006/0271129 A1* | 11/2006 | Tai | ........................... | A61N 2/02 607/61 |
| 2008/0008344 A1* | 1/2008 | Wakabayashi | ......... | G02C 11/06 381/327 |
| 2009/0002626 A1* | 1/2009 | Wakabayashi | ......... | G02C 11/06 351/116 |
| 2013/0242262 A1* | 9/2013 | Lewis | ................ | G02B 27/0093 351/209 |
| 2015/0153825 A1* | 6/2015 | Lee | .................... | G02B 27/0172 345/8 |
| 2017/0027812 A1* | 2/2017 | Hyde | .................. | A61H 23/004 |
| 2018/0289960 A1* | 10/2018 | Black | ....................... | A61F 7/12 |

FOREIGN PATENT DOCUMENTS

| | | | | |
|---|---|---|---|---|
| KR | 200416313 Y1 * | 5/2006 | | |
| KR | 10-1285364 | 7/2013 | | |
| KR | 10-1485704 | 1/2015 | | |
| WO | WO-2016176668 A1 * | 11/2016 | ............ | A61B 7/003 |
| WO | WO 2016/190685 | 12/2016 | | |

\* cited by examiner

[FIG 1]
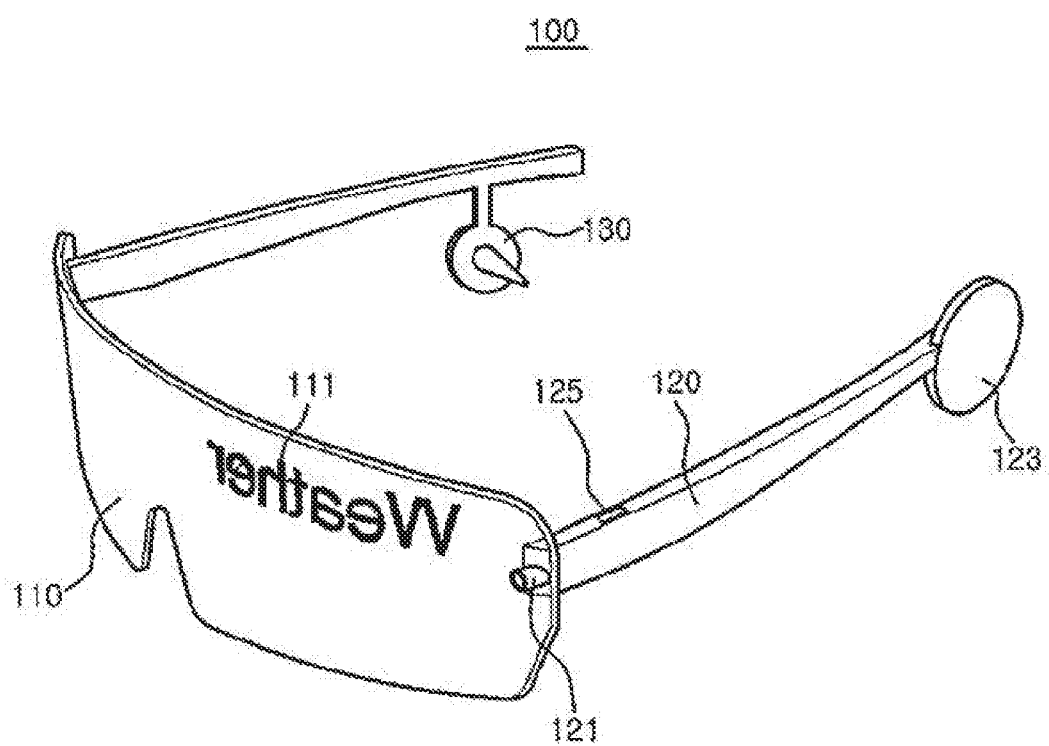

[FIG 2]
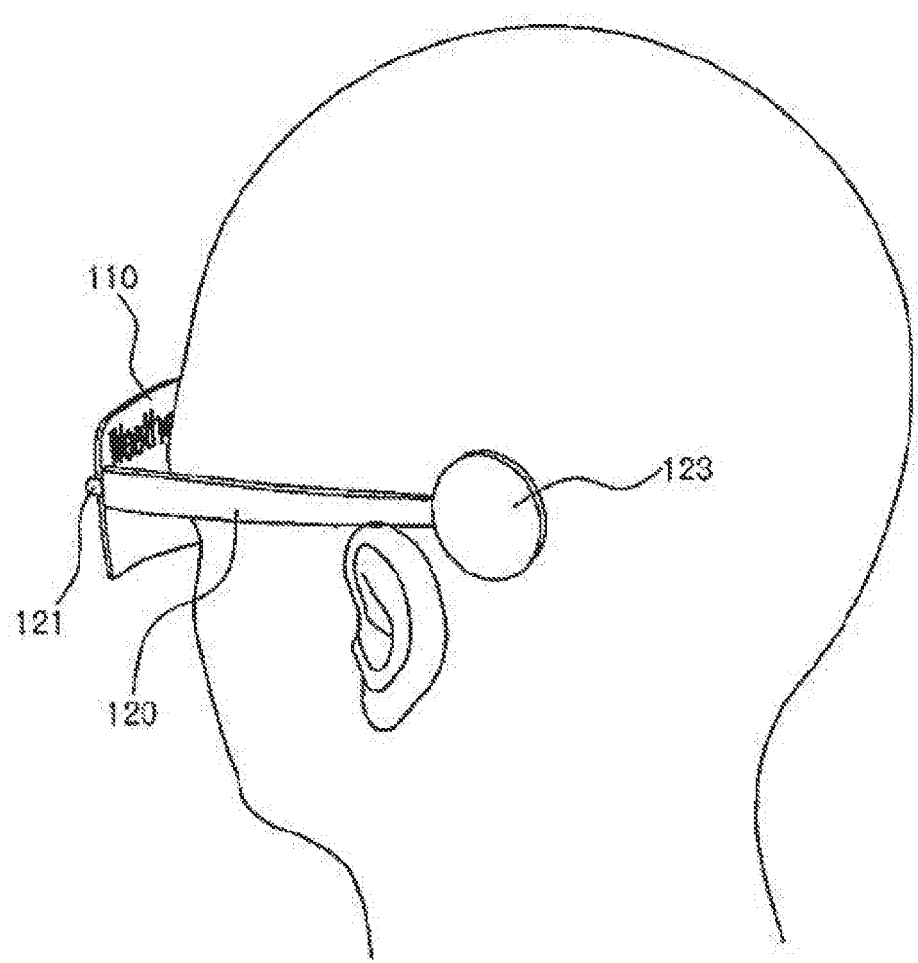

[FIG 3]
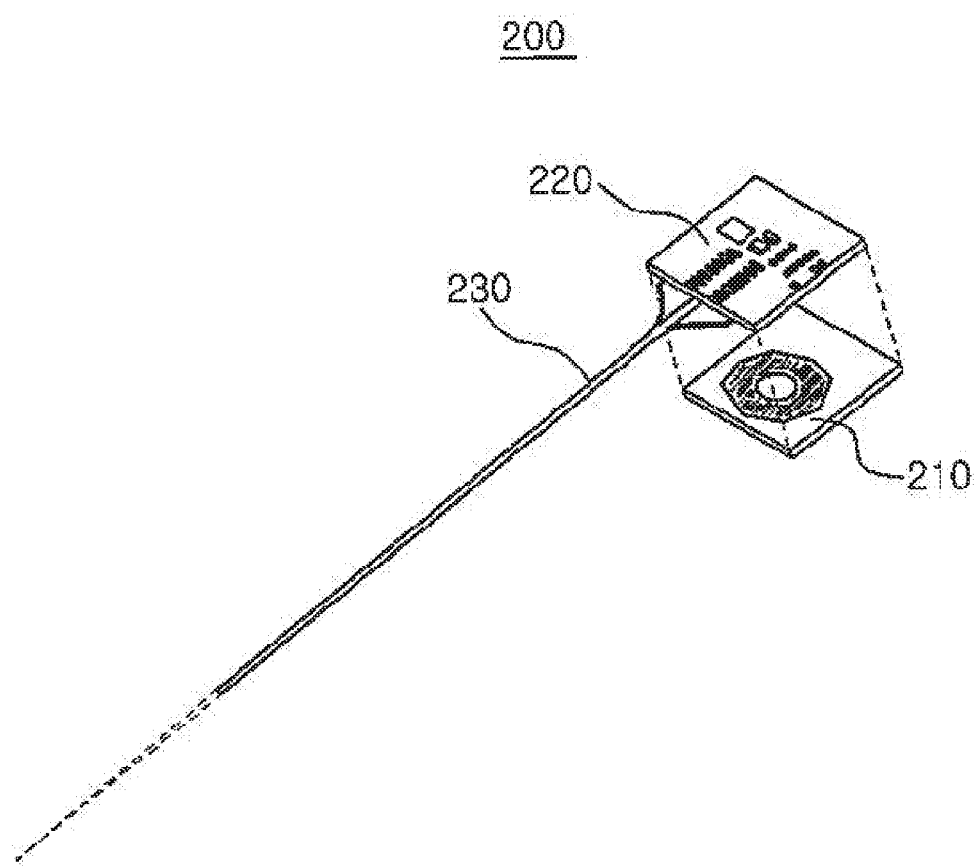

[FIG 4]
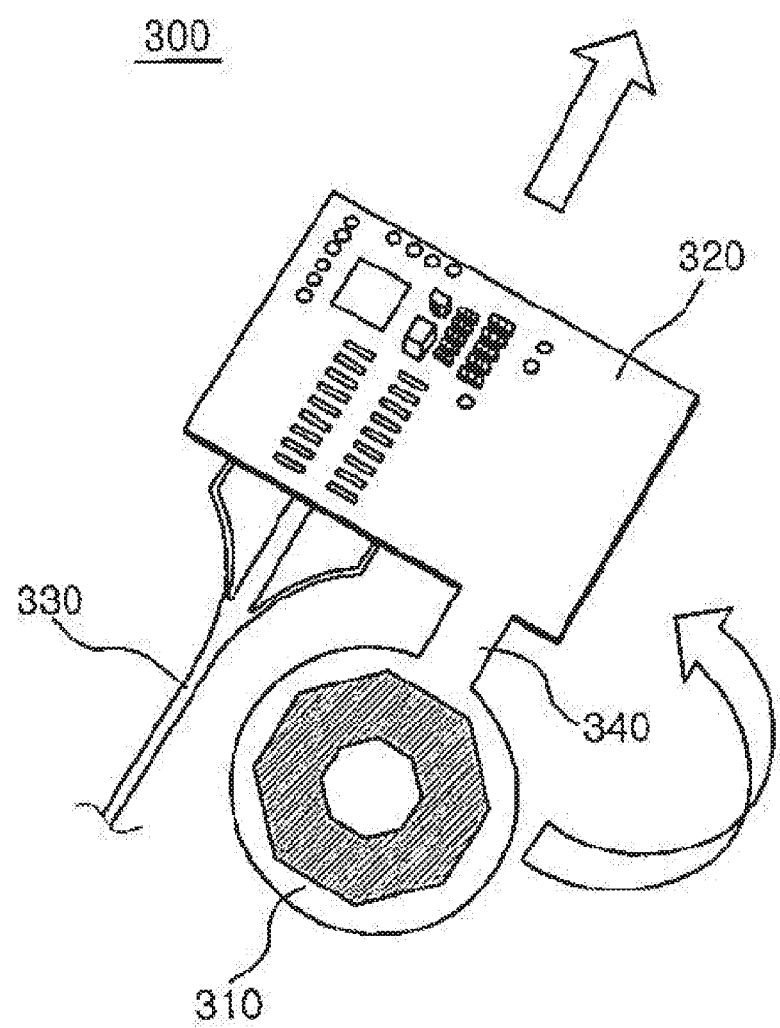

[FIG 5]
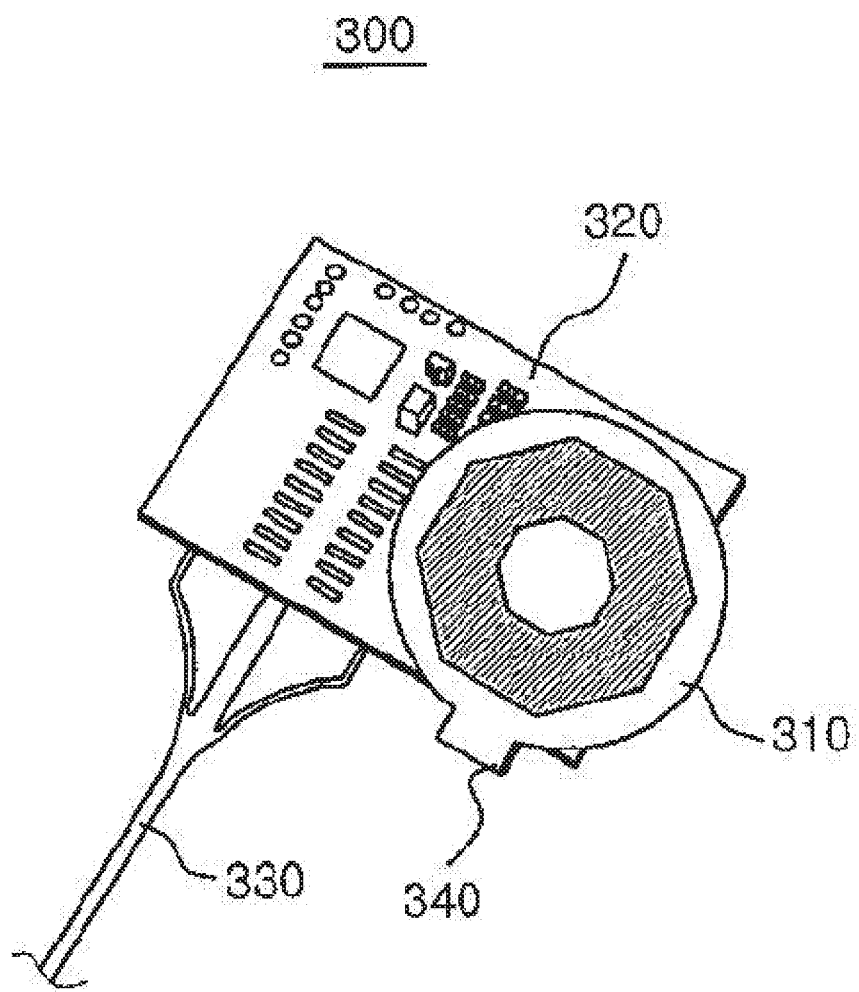

GLASSES-SHAPED COCHLEAR IMPLANT DEVICE

FIELD AND BACKGROUND OF THE INVENTION

Related Applications

This application is a National Phase of PCT Patent Application No. PCT/KR2016/005589 having International filing date of May 26, 2016, which claims the benefit of priority of Korean Patent Application No. 10-2015-0073066 filed on May 26, 2015. The contents of the above applications are all incorporated by reference as if fully set forth herein in their entirety.

Cochlear implant devices disclosed in the art include a behind-the-ear type, a body-worn type, and the like.

Such well-known cochlear implant devices include an external device and an implantable device. The external device provides an electrical signal and power, which correspond to a collected sound signal, to the implantable device. The implantable device delivers an electrical pulse generated by demodulating the electrical signal to an auditory organ.

Such a cochlear implant device normally operates only when the external device located outside the body delivers an electrical signal and power to the implantable device located inside the body. Thus, a transmission coil is provided in the external device, and a receiver coil is provided in the implantable device.

Furthermore, alignment of the transmission coil and the receiver coil is important to efficiently transmit signals between the transmission coil of the external device and the receiver coil of the implantable device, and therefore a magnet is used.

However, since the magnet is used for alignment of the transmission coil and the receiver coil, there is a possibility of skin damage due to continuous mechanical pressure on the skin.

Furthermore, in a magnetic resonance environment, in addition to a phenomenon in which the device is dragged by the magnet, image distortion may also occur. Therefore, there was a problem in that recipients of cochlear implants had limited access to a magnetic resonance imaging (MRI) device.

Summary Of The Invention

Accordingly, the present invention is directed to providing a cochlear implant device with a glasses shape which is designed to have the glasses shape for improving body wearability and an aesthetic feature. The present invention is also directed to providing a cochlear implant device with a glasses shape in which a transmission coil is integrally provided at an end of a glasses temple so that a region of the body with which the transmission coil comes into contact is changed according to a bending degree of the glasses temple. Such a glasses-shaped cochlear implant device allows a receiver coil implanted in the body to be aligned with a transmission coil outside the body without using a magnet.

One aspect of the present invention provides a cochlear implant device with a glasses shape including: a glasses lens part that rests near a nasal bridge of a body when the device is worn; glasses temples having a microphone for collecting a sound signal is provided at one thereof, wherein the glasses temples are flexible and are integrally coupled to the glasses lens part; a signal processor which is embedded in the glasses temple, processes the sound signal collected by the microphone, and generates an electrical signal, a battery which is embedded in the glasses temple and supplies power to the microphone and the signal processor, and a transmission coil integrally provided at an end of the one of the glasses temples which is located at a side opposite a side at which the glasses temples are coupled to the glasses lens part so that a region of body with which the transmission coil comes into contact is changed according to a bending degree of the glasses temple, and configured to provide the electrical signal generated by the signal processor and power supplied by the battery to an auditory organ stimulator which is implantable in the body.

The auditory organ stimulator may include a receiver coil which receives the electrical signal and the power from the transmission coil, a pulse generator which demodulates the electrical signal provided by the receiver coil and generates an electrical pulse corresponding to the sound signal, and an electrode which delivers the electrical pulse generated by the pulse generator to a cochlea and stimulates the cochlea.

The receiver coil may be integrated at a first substrate, the pulse generator may be integrated on a second substrate, and the first substrate and the second substrate may be stacked.

The receiver coil may be integrated at a first substrate, the pulse generator may be integrated on a second substrate, and the first substrate and the second substrate may be connected by a flexible hinge member.

The cochlear implant device may further include a complete-in-canal speaker which reproduces the electrical signal generated by the signal processor.

The cochlear implant device may further include an interfacing terminal provided at the glasses temple and used for wired communication or wireless communication with a computer.

The cochlear implant device may further include a display device which is integrated on a lens of the glasses lens part and outputs visual data.

According to embodiments of the present invention, a cochlear implant device is designed to have a glasses shape so that body wearability and aesthetic features are improved.

Furthermore, since a transmission coil is integrally provided at an end of a glasses temple such that a region of the body with which the transmission coil comes into contact is changed according to a bending degree of the glasses temple, alignment between a receiver coil implanted into the body and the transmission coil outside the body can be achieved without using a magnet.

Therefore, there is no possibility of skin damage because mechanical pressure continuously applied to skin by a magnet is fundamentally prevented. Furthermore, in a magnetic resonance environment, in addition to the phenomenon in which the device is dragged by the magnet, image distortion is also prevented. Therefore, a magnetic resonance imaging device is not limited even for a recipient of a cochlear implant device.

BRIEF DESCRIPTION OF THE SEVERAL VIEWS OF THE DRAWINGS

FIG. 1 is a block diagram of an external device of a cochlear implant device with a glasses shape according to one embodiment of the present invention.

FIG. 2 is a diagram illustrating a state of wearing the external device of the cochlear implant device with a glasses shape according to one embodiment of the present invention.

FIG. 3 is a configuration diagram illustrating an example of an auditory organ stimulator serving as an implantable device of the cochlear implant device with a glasses shape according to one embodiment of the present invention.

FIGS. 4 and 5 are configuration diagrams illustrating other examples of the auditory organ stimulator serving as an implantable device of the cochlear implant device with a glasses shape according to one embodiment of the present invention. FIG. 4 illustrates a receiver coil before folding, and FIG. 5 illustrates the receiver coil after folding.

DESCRIPTION OF SPECIFIC EMBODIMENTS OF THE INVENTION

The advantages and characteristics of the present invention and the methods of accomplishing the same may be clearly understood with reference to the detailed description of exemplary embodiments to be described and the accompanying drawings. However, the present invention is not limited to the exemplary embodiments disclosed below, and may be implemented in many different forms. The exemplary embodiments are merely provided to complete the disclosure of the present invention and fully convey the scope of the present invention to those of ordinary skill in the art, and the present invention should be defined only by the accompanying claims. Throughout the specification, like numerals denote like elements.

In the description of the present invention, when it is determined that detailed descriptions of related well-known functions or configurations unnecessarily obscure the gist of the present invention, such detailed descriptions will be omitted. Terms described below are defined in consideration of functions in the present invention and meanings may vary depending on a user's or operator's intentions or customs. Therefore, the meanings of the terms should be interpreted based on the scope throughout this specification.

FIG. 1 is a block diagram of an external device of a cochlear implant device with a glasses shape according to one embodiment of the present invention, and FIG. 2 is a diagram illustrating a state of wearing the external device of the cochlear implant device with a glasses shape according to one embodiment of the present invention.

As shown in the drawings, an external device 100 of the cochlear implant device according to one embodiment of the present invention may include a glasses lens part 110 which rests near a nasal bridge of a body when the external device is worn. In addition, a display device 111 for outputting visual data is integrated on a lens of the glasses lens part 110. For example, the display device 111 may be implemented as a film-type liquid crystal display (LCD).

In addition, the external device 100 includes glasses temples 120 which are flexible and are integrally coupled to the glasses lens part 110 and a microphone 121 for collecting a sound signal provided at one of the glasses temples 120.

Furthermore, the external device 100 includes a signal processor (not shown) for processing a sound signal collected by the microphone 121 and generating an electrical signal, wherein the signal processor (not shown) is embedded in the glasses temple 120. For example, the signal processor (not shown) may be implemented as a processor such as a central processing unit (CPU) or the like.

Furthermore, the external device 100 includes a battery (not shown) for supplying power to the microphone 121, the signal processor (not shown), and a transmission coil 123, wherein the battery (not shown) is embedded in the glasses temple 120.

Here, the signal processor (not shown) and the battery (not shown) may be embedded in the glasses temple 120 while being integrated in a single module.

Further, the external device 100 includes the transmission coil 123 to provide the electrical signal generated by the signal processor (not shown) and the power supplied by the battery (not shown) to an auditory organ stimulator 200 (see FIG. 3) or 300 (see FIGS. 4 and 5) which is implantable in a body. The transmission coil 123 is integrally provided at an end of the one of the glasses temples 120, wherein the end is located at a side opposite a side at which the glasses temples 120 are coupled to the glasses lens part 110. A region in which the transmission coil 123 comes into contact with the body is changed according to a bending degree of the glasses temple 120.

Furthermore, the external device 100 includes an interfacing terminal 125 used for wired communication or wireless communication with a computer, wherein the interfacing terminal 125 is provided at the glasses temple 120. For example, the interfacing terminal 125 may be implemented as a Universal Serial Bus (USB) terminal or the like.

In addition, the external device 100 may further include a complete-in-canal speaker 130. The complete-in-canal speaker 130 may be manufactured in a shape in which the complete-in-canal speaker 130 is supported by the glasses temple 120 while being integrally connected to the glasses temple 120. When the signal processor (not shown) processes a sound signal collected by the microphone 121 and generates an electrical signal, the complete-in-canal speaker 130 serves to reproduce the electrical signal.

FIG. 3 is a configuration diagram illustrating an example of the auditory organ stimulator serving as an implantable device of the cochlear implant device with a glasses shape according to one embodiment of the present invention.

As shown in the drawing, an auditory organ stimulator 200 according to one embodiment of the present invention includes a receiver coil 210 which receives an electrical signal and power from the transmission coil 123 (see FIG. 1).

Furthermore, the auditory organ stimulator 200 includes a pulse generator 220 for demodulating an electrical signal provided by the receiver coil 210 and generating an electrical pulse corresponding to a sound signal.

In addition, the auditory organ stimulator 200 includes an electrode 230 which delivers the electrical pulse generated by the pulse generator 220 to a cochlea of the body to stimulate the cochlea.

The auditory organ stimulator 200 includes a structure in which the receiver coil 210 is integrated on a first substrate, the pulse generator 220 is integrated on a second substrate, and the first substrate and the second substrate are stacked.

FIGS. 4 and 5 are configuration diagrams illustrating other examples of the auditory organ stimulator serving as an implantable device of the cochlear implant device with a glasses shape according to one embodiment of the present invention. FIG. 4 illustrates a receiver coil before folding, and FIG. 5 illustrates the receiver coil after folding. As shown in the drawings, an auditory organ stimulator 300 according to one embodiment of the present invention includes a receiver coil 310 which receives an electrical signal and power from the transmission coil 123 (see FIG. 1).

Furthermore, the auditory organ stimulator 300 includes a pulse generator 320 for demodulating an electrical signal provided by the receiver coil 310 and generating an electrical pulse corresponding to a sound signal.

In addition, the auditory organ stimulator 300 includes an electrode 330 which delivers the electrical pulse generated by the pulse generator 320 to a cochlea of the body to stimulate the cochlea.

The auditory organ stimulator 300 includes a structure in which the receiver coil 310 is integrated on a first substrate, the pulse generator 320 is integrated on a second substrate, and the first substrate and the second substrate are connected by a flexible hinge member 340.

According to one embodiment of the present invention, the external device 100 of the cochlear implant device is designed to have a glasses shape, and thus discomfort caused by wearing an individual device is minimized, and hearing impairment is not externally visible.

The microphone 121 is integrated on the glasses temple 120 of a glasses frame to collect a sound signal.

Furthermore, a signal processor (not shown) for processing a sound signal collected by the microphone 121 and generating an electrical signal is embedded in the glasses temple 120 with the battery (not shown). Here, the signal processor (not shown) and the battery (not shown) may be integrally modularized.

Upgrade of software which is provided in the signal processor (not shown) for operating and driving the signal processor (not shown), that is a program executable by a computer, may be performed using the interfacing terminal 125 provided at the glasses temple 120. Furthermore, the battery (not shown) may be charged through the interfacing terminal 125. In addition, wired communication or wireless communication with a computer, such as a personal computer, a smartphone, a tablet device, etc., may be performed using the interfacing terminal 125. A computer, a smartphone, a tablet device, or the like may map identification information granted to the external device 100 of the cochlear implant device and identification information of a person wearing the external device 100 of the cochlear implant device, and control or manage the external device 100 of the cochlear implant device through wired communication or wireless communication with the external device 100 of the cochlear implant device.

The electrical signal generated by the signal processor (not shown) and the power from the battery (not shown) are delivered to the auditory organ stimulator 200 or 300 through the transmission coil 123 located at an end part of the glasses temple 120.

The transmission coil 123 may be required to adjust a location for alignment with the auditory organ stimulator 200 or 300. According to the embodiments of the present invention, because the transmission coil 123 is integrally provided at the end of the glasses temple 120, a location of the body with which the transmission coil 123 comes into contact is changed according to the bending degree of the glasses temple so that alignment with the auditory organ stimulator 200 or 300 is achieved.

The sound signal collected by the microphone 121 provided at the glasses temple 120 is delivered to the signal processor (not shown) embedded in the glasses temple 120, and the signal processor (not shown) generates an electrical signal corresponding to the sound signal. In addition, the generated electrical signal may be displayed as a caption, a keyword, a graphic, or the like through the display device 111 integrated on the lens of the glasses lens part 110 and provide an individual visual cue to a user of a cochlear implant.

An advantage of the cochlear implant device is maximized when the cochlear implant device is used with a polymer-based compact auditory organ stimulator 200 or 300 in a compatible manner. As a polymer, a polyimide, a parylene (parylene-C), a liquid crystal polymer, or the like with high biocompatibility and a low water absorption rate may be used. When a polymer is used, a compact receiver coil 210 and 310 may be integrated on a polymer substrate with a material having high conductivity such as copper using a microelectromechanical system (MEMS) technique, and may be packaged with a polymer. In this case, because communication efficiency is high and alignment between the transmission and receiver coils is not sensitive to errors, coil communication is possible merely by determining an approximate location without a magnet for alignment. Therefore, according to the embodiments of the present invention, the necessity of coil attachment using a magnet is removed, and therefore MRI compatibility of the cochlear implant device is completely ensured.

For a patient who needs cochlear implantation in both right and left ears (bilateral cochlear implant), the transmission coil 123 is placed at each of the glasses temples 120. In this way, wearing the external device 100 having a glasses shape is sufficient for use the cochlear implant device on one or both of the glasses temples 120. Therefore, discomfort caused by wearing the existing device and a problem of revealing impairment can be overcome.

The auditory organ stimulator 200 or 300 demodulates electrical signal data received from the external device 100 to generate an electrical pulse and delivers the generated electrical pulse to a multi-channel electrode 230 or 330 implanted in a cochlea of the body. An auditory nerve is stimulated by the electrical pulse so that a sound is electrically recognizable.

Titanium is used for a packaging material of a cochlear implant device according to the related art, and a receiver coil is located in a space separated from the titanium package, is coated with a silicone elastomer, and is aligned with a transmission coil of an external device through a magnet. Here, since the receiver coil is located outside the titanium package and is coated with the silicone elastomer having a high water absorption rate, the receiver coil is made of a material with high biocompatibility like platinum or gold but relatively low conductivity. Therefore, communication efficiency decreases between the transmission and receiver coils, and alignment between the transmission and receiver coils is significant.

According to the embodiments of the present invention, the auditory organ stimulator 200 or 300 is made of a polymer (polyimide, parylene, liquid crystal polymer, etc.), and because the receiver coil 210 and 310 is packaged with the polymer, the coil may be manufactured with a material with high communication efficiency such as copper. When a flat-type coil which is patterned by a MEMS technique on a polymer substrate is used, a compact coil is usable. When the auditory organ stimulator 200 or 300 with such a polymer substrate and the external device 100 in a glasses shape are interfaced with each other, communication is possible using the transmission coil 123 located in the glasses temple 120 without using a magnet for alignment. Accordingly, MRI safety and compatibility are completely ensured.

When a distance between the transmission coil 123 of the external device 100 and the receiver coil 210 or 310 of the auditory organ stimulator 200 or 300 needs to be slightly closer or locations need to be partially adjusted, the auditory organ stimulator 300 and the receiver coil 310 exemplified in FIGS. 4 and 5 may be used.

The pulse generator 320 of the auditory organ stimulator 300 is located on a temporal bone (drilled on a portion of a temporal bone, if necessary), and the flexible hinge member 340 is folded as shown in FIG. 5 so that the receiver coil 310 may be located on a temporalis or under the skin. When the receiver coil 310 and the hinge member 340 are implemented on a flexible polymer substrate, the receiver coil 310 and the hinge member 340 are easily bent or folded.

Therefore, when the auditory organ stimulator 300 and the receiver coil 310 are used, a sufficient communication distance is ensured even for a recipient with thick skin or a developed temporalis.

Further, because the glasses temples 120 are located at both of right and left sides, it is applicable to a bilateral cochlear implant without an additional external processing device being worn. Further, when the complete-in-canal speaker 130 is included in the external device 100, it is applicable to an electric acoustic stimulation (EAS) which delivers a sound stimulation signal and an electrical stimulation signal to an end side using a hearing aid and a cochlear implant.

In addition, when a visual cue, such as a caption, a keyword, a graphic, etc., is provided using the display device 111 integrated on the lens of the glasses, it is possible to contribute to an increase in a recognition rate under noise, and assist language rehabilitation training after a cochlear implantation.

Although the above embodiments have been described with reference to a number of illustrative embodiments of the present invention, it should be understood that numerous other modifications and embodiments can be devised by those skilled in the art that will fall within the spirit and scope of the principles of this disclosure. The embodiments disclosed herein, therefore, are not to be taken in a sense for limiting the technical concept of the present invention but for explanation thereof, and the range of the technical concept is not limited to these embodiments. The scope of the present invention should be construed by the appended claims, along with the full range of equivalents to which such claims are entitled.

What is claimed is:

1. A cochlear implant device with a glasses shape, comprising:
    an auditory organ stimulator configured to be implanted in a user's head; and
    an external device for wirelessly communicating with the auditory organ stimulator, the external device comprising:
        a glasses lens part;
        glasses temples coupled to the glasses lens part;
        a microphone disposed in one of the glasses temples and collecting a sound signal;
        a signal processor embedded in one of the glasses temples and processing the sound signal collected by the microphone, and generates an electrical signal;
        a battery disposed in the glasses temple and supplies power to the microphone and the signal processor; and
        a transmission coil coupled to an end portion of one of the glasses temples,
        wherein the transmission coil is configured to provide the electrical signal generated by the signal processor and the power supplied by the battery to the auditory organ stimulator,
    wherein the auditory organ stimulator includes:
        a receiver coil configured to receive the electrical signal and the power from the transmission coil;
        a pulse generator configured to demodulate the electrical signal provided by the receiver coil and generate an electrical pulse corresponding to the sound signal; and
        an electrode configured to deliver the electrical pulse generated by the pulse generator to a cochlea and stimulate the cochlea,
    wherein the receiver coil is integrated on a first flexible polymer substrate;
    wherein the pulse generator is integrated on a second flexible polymer substrate; and
    the first flexible polymer substrate and the second flexible polymer substrate are connected by a flexible hinge member extended therebetween along an extension axis,
    the first flexible polymer substrate includes an upper surface and a lower surface and the second flexible polymer substrate includes an upper surface and a lower surface,
    wherein the glasses temple to which the transmission coil is coupled is bendable, such that, when the auditory organ stimulator is implanted in the user's head, a position of the transmission coil relative to the receiver coil is adapted to change according to a bending degree of said glasses temple;
    wherein the transmission coil provides the electrical signal and the power to the auditory organ stimulator only when the transmission coil and receiver coil are aligned, and the auditory organ stimulator does not include a magnet for alignment of the receiver coil with the transmission coil;
    wherein the second flexible polymer substrate comprises a first side surface connecting to the electrode, the flexible hinge member is disposed between the first side surface and the first flexible polymer substrate;
    wherein an extending direction of the electrode is parallel to the extension axis of the flexible hinge member;
    wherein a gap is formed between the electrode and the flexible hinge member;
    wherein the first flexible polymer substrate is disposed on the second flexible polymer substrate and the upper surface of the first flexible polymer substrate faces the upper surface of the second flexible polymer substrate by bending of the flexible hinge member; and
    wherein the upper surface of the second flexible polymer substrate comprises a first portion on which a plurality of electric components is disposed and a second portion on which the first flexible polymer substrate is disposed and electronic component is not disposed.

2. The cochlear implant device of claim 1, further comprising a complete-in-canal speaker configured to reproduce the electrical signal generated by the signal processor.

3. The cochlear implant device of claim 1, further comprising an interfacing terminal provided at the glasses temples and used for wired communication or wireless communication with a computer.

4. The cochlear implant device of claim 1, further comprising a display device which is integrated on a lens of the glasses lens part and outputs visual data.

5. The cochlear implant device of claim 2, wherein the cochlear implant device is used for an electric acoustic stimulation (EAS) by delivering a sound stimulation signal using the complete-in-canal speaker and the electrical signal as an electrical stimulation signal.

6. The cochlear implant device of claim 1, wherein the receiver coil is comprised of copper and is patterned on the first polymer substrate using a microelectromechanical system technique.

* * * * *